United States Patent [19]

Hickner

[11] 3,968,167

[45] July 6, 1976

[54] METHYLOL DERIVATIVES OF POLYTHIOLS

[75] Inventor: Richard A. Hickner, Lake Jackson, Tex.

[73] Assignee: The Dow Chemical Company, Midland, Mich.

[22] Filed: Sept. 15, 1975

[21] Appl. No.: 613,716

Related U.S. Application Data

[63] Continuation-in-part of Ser. No. 548,115, Feb. 7, 1975, abandoned, which is a continuation-in-part of Ser. No. 388,714, Aug. 16, 1973, abandoned.

[52] U.S. Cl. .................... 260/609 F; 260/609 D; 260/609 E; 260/2 EP; 260/47 EP
[51] Int. Cl.² ............................................. C07C 149/26
[58] Field of Search .......... 260/609 D, 609 E, 2 EP, 260/47 EP

[56] References Cited

UNITED STATES PATENTS

| | | | |
|---|---|---|---|
| 3,716,588 | 2/1973 | Esclamadon et al............ | 260/609 R |
| 3,718,700 | 2/1973 | Esclamadon et al............ | 260/609 R |

FOREIGN PATENTS OR APPLICATIONS

| | | | |
|---|---|---|---|
| 1,487,364 | 7/1967 | France............................ | 260/609 A |

*Primary Examiner*—Lewis Gotts
*Assistant Examiner*—D. R. Phillips
*Attorney, Agent, or Firm*—Albin R. Lindstrom

[57] ABSTRACT

Formaldehyde is reacted with a polythiol to give novel methylol derivatives of the polythiol. The methylol derivatives are useful in curing polyepoxides.

2 Claims, No Drawings

3,968,167

METHYLOL DERIVATIVES OF POLYTHIOLS

U.S. Pat. No. 3,734,968. In that application the polythiols are defined as those of the formula

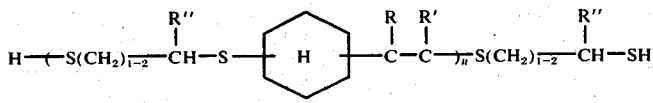

CROSS-REFERENCE TO COPENDING APPLICATION

This application is a continuation-in-part of my copending application U.S. Ser. No. 548,115 filed Feb. 7, 1975 now abandoned which was a continuation-in-part of U.S. Ser. No. 388,714 filed Aug. 16, 1973 (now abandoned).

BACKGROUND OF THE INVENTION

This invention presents highly reactive polyfunctional substances that are coreactive with polyepoxides. Polythiols are known to react with polyepoxides to form useful cured resins. However, polythiols are also known to possess undesirable odors. That characteristic has frequently precluded their use. The present invention provides products having the polythiol reactivity with polyepoxides but with little odor.

PRIOR ART

The reactivity of a thiol group with an oxirane function is well known and is pointed out in standard reference works.

U.S. Pat. No. 3,278,496 is typical of a number of patents showing the reaction. In that patent thiol terminated polyoxyalkylene glycols are coreacted with polyepoxides.

U.S. Pat. No. 3,718,700 teaches thiol terminated thiols that represent the problem solved by the present invention.

The reaction of a thiol with formaldehyde is indicated in U.S. Pat. No. 3,716,588 and in Walker, "Formaldehyde", Reinhold Publishing Corporation, New York, ACS Monograph Series, Pages 279–280 wherein a methylol derivative of a thiol is postulated to be the reaction product of a mercaptan and formaldehyde.

DESCRIPTION OF THE INVENTION

The methylol derivatives of this invention are prepared by reacting formaldehyde with a polythiol. Any compound having two or more mercaptan groups per molecule may be methylolated and thereby retain its reactivity to polyepoxides but with a greatly reduced odor. Although hydroxyl compounds are known to react at elevated temperatures with oxirane compounds, the room temperature reaction is sluggish at best, the methylol derivatives of this invention are highly reactive at room temperature.

One class of polythiols that may be used in making the methylol derivatives is described and claimed in wherein $n$ is 1–3, one of R and R' is hydrogen and the other is hydrogen or methyl, and R" is hydrogen or methyl. Cogeneric mixtures of compounds within the formula are also taught. The compounds are indicated to be highly reactive with polyepoxides.

Another class of polythiols having high reactivity with polyepoxides is described and claimed in the copending application of Hickner et al. U.S. Ser. No. 245,185 filed Apr. 18, 1972. In that application the polythiols are defined as those cycloaliphatic polythiols of the formula

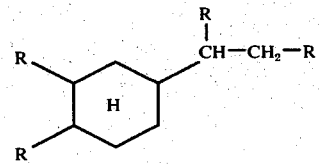

wherein each R is —Cl, —Br, —SR$_1$SH or OR$_2$SR$_1$SH provided that at least two of said R groups have a terminal thiol group; R$_1$ is an alkylene group of 2 to 10 carbon atoms or an alkylene group of 2 to 10 carbon atoms having one or more —O— or —S— ether groups and R$_2$ is an alkylene group of 2 to 4 carbon atoms.

The methylol derivatives resulting from reacting formaldehyde with the above polythiols, have the formula:

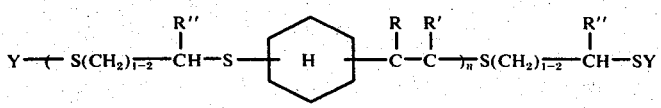

wherein $n$ is 1–3, one of R and R' is hydrogen and the other is hydrogen or methyl, and R" is hydrogen or methyl; or have the formula

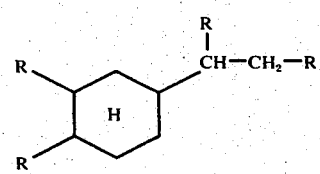

wherein each R is —Cl, —Br, —SR$_1$SY or —OR$_2$SR$_1$SY provided that at least two of said R groups independently are of said —SR$_1$SY or —OR$_2$SR$_1$SY; R$_1$ is an alkylene group having 2 to 10 carbon atoms or an alkylene group having 2 to 10 carbon atoms having one or more —O— or —S— ether groups and R$_2$ is an alkylene group of 2 to 4 carbon atoms; and wherein at least one Y is —CH$_2$OH with any remaining Y substituents being hydrogen.

Because of their reactivity with polyepoxides and the desirability of the resulting cured products, the above classes of polythiols are preferred for use in this invention. However, other polythiols including those of relatively simple structure, such as the alkane dithiols of which 1,4-butane dithiol is representative, to complex dithiols may likewise be methylolated in accordance with the invention. The only requirement is that the compound have at least two mercaptan groups and be free of other groups reactive with formaldehyde under the conditions of methylolation.

Processes for the preparation of the more complex polythiols are known. In one typical preparation, an alkane dithiol is reacted with a polyene such as vinyl cyclohexene. The reaction of formaldehyde with the polythiol proceeds smoothly under mild reaction conditions of elevated temperature of about 80°–90°C. for a few hours. Lower or higher temperatures may be used with a corresponding change in time of reaction.

Paraformaldehyde may be employed with equal facility as the conventional aqueous solutions of formaldehyde.

The benefits and advantages of the present invention are available from the product obtained when aldehyde reactant is supplied in fully stoichiometric amounts and the reaction is carried forward until all or substantially all thiol sites are modified by condensation with aldehyde to obtain a methylol terminal moiety. However, in some way that is not fully understood, the same advantages and benefits of very rapid cure of polyepoxide under even adverse conditions of temperature are present also when the aldehyde is supplied in amounts less, and even amounts very much less, than stoichiometric. Thus, when one equivalent of aldehyde is provided for each ten thiol equivalents, the resulting product can be regarded as having 10 percent capped thiol sites. Even so, it has the rapid, relatively low-temperature curing properties obtained in related other product prepared by employing higher amounts of the aldehyde. Similarly, the advantages and benefits of the present invention are measurably present when aldehyde is supplied in an amount equivalent to approximately one-twentieth that stoichiometric with the mercaptomethyl substituents.

The products of the present invention are useful as reactive curing agents with polyepoxide substances to obtain cured articles. The present substances in the presence of suitable catalyst, react smoothly and successfully to obtain a fully cured epoxy resin at temperatures as low as minus 20°C. Room temperature cure occurs quite rapidly, taking place, depending upon the precise mixture employed and other matters, typically in a period of an hour or less. At a curing temperature of approximately 40°F., complete cure sometimes takes place in only a very few minutes.

As is common experience in the epoxy resin field, the superior curing agent of this invention can be employed to cure any 1,2-polyepoxide starting material to obtain an epoxy resin. The reactivity of the oxirane ring and presence of an average of more than one such ring per molecule are the critical aspects of the polyepoxide, common to all curable such substances, by means of which the cure of the present invention functions.

It is therefore convenient to choose the starting curable polyepoxide on the basis of its known properties. When it is desired to obtain a colorless or nearly colorless glass-hard cured product, a polyglycidyl ether of a bisphenol may be the starting polyepoxide of choice.

When it is desired to obtain a substance which is flame resistant and fire-retardant, a brominated polyepoxide starting material may be chosen. Similarly, other polyepoxides can be chosen on the basis of the known properties which they confer upon the resulting cured resins, such as high adhesivity to vitreous surfaces, flexibility in the resulting resin, water solubility if desired and the like.

More particularly, the instant curing agents are useful in curing the polyglycidyl ethers of the bisphenols and the longer chain polyethers derived from further etherification with further bisphenol and oxyalkyloxy moieties of the same, the polyether product in each instance terminating with a 1,2-epoxy lower alkoxy structure presenting the reactive oxirane ring characteristic of the polyepoxide materials. Similarly, the present curing agent successfully cures the epoxy novolak substances to obtain cured resins of great density and high cross-linking. Also, when it is desired to obtain a flexible epoxy resin the present curing agent is used in conjunction with an epoxylated polyglycol prepared by the etherification of terminal hydroxyls of a poly lower alkylene glycol of any desired molecular weight from approximately 200 to approximately 25,000 with 1,2-epoxy lower alkoxy moieties. Further, when it is desired to obtain a cured resin which is flame retardant and of low inherent flammability, a brominated polyepoxide is chosen and is cured satisfactorily with the present curing agent. Mixed brominated and unbrominated polyepoxides can be used.

In common with many epoxy resin curing agents, the curing agent of the present invention is assisted by the presence of small, catalytic amounts of an epoxy resin curing catalyst. Virtually any known epoxy resin curing catalyst may be employed; however, tertiary amines are the preferred catalysts.

Benzyl dimethyl amine is such a material. Tetramethyl guanidine gives very rapid cures. A complex of boron trifluoride with monoethyl amine is another as is also dicyandiamide. Also dimethylaminomethyl phenol is available as is tris(dimethylaminomethyl)phenol. Another such catalytic material is alphamethylbenzyldimethylamine and a phosphate zinc octoate composition commercially known as "DB VIII". Tertiary amines, generally, amine salts and other complexes which exhibit boron trifluoride in a physically stable form and amine borates are further available catalytic materials.

Moreover, the present curing agents function satisfactorily when the curable polyepoxide is caused to react with a reactive diluent or with a coreactive agent such as a monoglycidyl ether of any of numerous aromatic compounds, phenol, the drying oils, alkyd resins and the like. Also, curable polyepoxides to be cured by the use of the instant curing agent may satisfactorily be filled as with wood flour, silica, and all the various other known standard fillers to be used in conjunction with epoxy resins. Except that the curing agent to be employed is the particular product of this invention, and that the curing process enjoys various corresponding advantages, the procedures to be followed are those of the prior art and require no special skill.

EXAMPLE 1

54.3 Grams (0.3 equivalent) of a thiol prepared by reacting ethanedithiol with trivinylcyclohexane and having an SH equivalent weight of 175 and 25 grams (0.32 mole) of 37 percent aqueous formaldehyde were heated at 80°C. for 5 hours. The water was removed by evaporation at 40°C, and under reduced pressure. The product was a fairly viscous, cloudy liquid having an ethereal odor.

5.28 Grams of the above product, 4.73 grams of the diglycidyl ether of bisphenol A (E.E.W.=182–190) and 0.1 gram benzyl dimethylamine were mixed. A portion of the product was poured into an aluminum cup and another portion was used to cast a 5 mil film. Both samples were tack-free in less than 30 minutes at room temperature. The casting was a tough, tear-resistant material.

EXAMPLE 2

The formaldehyde adduct of Example 1 and the unmodified thiol prepared without formaldehyde were separately mixed with stoichiometric quantities of diglycidyl ether of bisphenol A and 2 parts per hundred parts of diglycidylether of benzyldimethylamine. The solutions were applied to a ½ × 1 inch area of 1 × 4 × 0.64 inch 2024T-3 aluminum coupons, which had been etched with chromic acid solution, and allowed to cure for 48 hours at room temperature. Separate portions of the above liquids were also applied to 1 × 12 inches × 3 mil of aluminum foil which had been washed with methylene chloride. The 1 × 4 coupons were tested for lap-shear strength according to ASTM D-100-2-64. The 1 × 12 inch strips were tested for peel strength according to ASTM D-1876-69.

|  | Peel (lbs./in) | Lap Shear (psi) |
|---|---|---|
| Unmodified thiol | 0.65 | 1475 |
| Formaldehyde adduct | 2.8 | 1870 |

The formaldehyde adduct was set 6 minutes after initial mixing. When a set of three coupons bonded with the formaldehyde adduct were allowed to cure at room temperature for 24 hours and subsequently post-cured for 1 hour at 100°C. the tensile shear strength was raised to 2500 psi.

EXAMPLE 3

A tetrathiol was prepared from an isomeric mixture of chlorides of the formula:

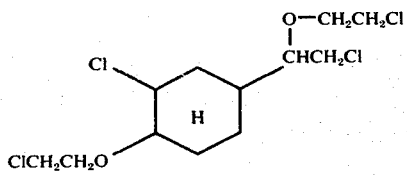

by the following procedure. In a 3 neck flask was placed a mixture of 282 grams (3 moles) of 1,2-ethanedithiol, 60 grams (1.5 moles) of NaOH, and 100 milliliters of isopropyl alcohol. The mixture was heated to reflux and 122 grams (1.5 chloride equivalents) of the above chloride was added dropwise over a 1 hour period and refluxed for an additional 20 hours. Water was then added to dissolve the sodium chloride and the solution neutralized with HCl. Two liquid layers formed. The lower layer was separated to recover the polythiol and heated at 110°C. at 0.1 mm in a flash still to remove excess ethanedithiol. The light yellow product weighed 291 grams, had a Gardner viscosity of A, had a thiol equivalent weight of 135 and had a residual chloride content of 5.7 percent.

137.5 Grams (one-SH equivalent) of polythiol and 57 grams (0.667 equivalent) of formaldehyde were charged to a flask and heated, with stirring, at 80°–85°C. for 4½ hours. The reaction mixture was then transferred to a Rinco evaporator and the water removed at reduced pressure while heating to 50°C. The product was a light yellow, liquid weighing 145 grams and having only a mild odor.

EXAMPLE 4

A 500 ml flask was charged with 222.8 grams (1 equivalent) of a dithiol (prepared by reacting 4-vinyl cyclohexene with ethanedithiol) and 40.5 grams (0.5 equivalent) of 37 percent formaldehyde. The mixture was heated at 83°C. for 3 hours. Xylene (100 ml) was added to the reaction product and then heated at reflux with an azeotrope head to remove the water. Final dehydration was accomplished by heating to 150°C. under full vacuum. The product was a colorless liquid with a Gardner viscosity of Y or 17.6 poises.

An adhesive formulation was prepared utilizing 4.75 grams (0.02 equivalent) of the above product, 0.44 gram (0.005 equivalent) of a polyamide curing agent, 0.1 gram of tetramethylguanidine, 0.1 gram of benzyl dimethylamine, 4.73 grams (0.025 equivalent) of diglycidyl ether of bisphenol A and sufficient ASP 400 aluminum silicate filler to give 47 percent by weight of filler. This adhesive was used to bond to pieces of fiberglass reinforced polyester.

EXAMPLE 5

A 500 ml flask was charged with 250 gram (0.5 equivalent) of a polythiol sold as Thiokol LP 3 and 20.25 grams (0.25 equivalent) of 37 percent formaldehyde. The mixture was heated at 83°C. for 3.5 hours and then treated as in Example 1. The product was a reddish liquid with only a slight thiol odor.

What is claimed is:

1. The methylol derivative of a polythiol, said derivative having the formula:

wherein $n$ is 1–3, one of R and R' is hydrogen and the other is hydrogen or methyl, and R'' is hydrogen or methyl; or said derivative having the formula

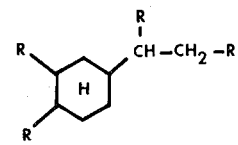

wherein each R is $-Cl$, $-Br$, $-SR_1SY$ or $-OR_2SR_1SY$ provided that at least two of said R groups independently are of said —SR$_1$SY or —OR$_2$SR$_1$SY; R$_1$ is an alkylene group having 2 to 10 carbon atoms or an alkylene group having 2 to 10 carbon atoms having one or more —O— or —S— ether groups and R$_2$ is an alkylene group of 2 to 4 carbon atoms; and wherein at least one Y is —CH$_2$OH with any remaining Y substituents being hydrogen.

2. The derivative of claim 1 wherein from 5 to 100 percent of the thiol groups are substituted with methylol.

* * * * *